US012035975B2

(12) United States Patent
An et al.

(10) Patent No.: US 12,035,975 B2
(45) Date of Patent: Jul. 16, 2024

(54) METHOD OF IDENTIFYING A SURGICALLY OPERABLE TARGET ZONE IN AN EPILEPTIC PATIENT'S BRAIN

(71) Applicants: UNIVERSITÉ D'AIX-MARSEILLE (AMU), Marseilles (FR); INSTITUT NATIONAL DE LA SANTÉ ET DE LA RECHERCHE MÉDICALE, Paris (FR)

(72) Inventors: Sora An, Marseilles (FR); Viktor Jirsa, Marseilles (FR)

(73) Assignees: UNIVERSITÉ D'AIX-MARSEILLE (AMU), Marseilles (FR); INSTIT NAT DE LA SANTÉ ET DE LA RECHERCHE MÉDICALE, Paris (FR)

( * ) Notice: Subject to any disclaimer, the term of this patent is extended or adjusted under 35 U.S.C. 154(b) by 405 days.

(21) Appl. No.: 17/614,450

(22) PCT Filed: May 27, 2020

(86) PCT No.: PCT/EP2020/064759
§ 371 (c)(1),
(2) Date: Nov. 26, 2021

(87) PCT Pub. No.: WO2020/239869
PCT Pub. Date: Dec. 3, 2020

(65) Prior Publication Data
US 2022/0249167 A1    Aug. 11, 2022

(30) Foreign Application Priority Data

May 27, 2019  (EP) .................................. 19176827

(51) Int. Cl.
*A61B 34/10*     (2016.01)
*A61B 5/00*      (2006.01)
(Continued)

(52) U.S. Cl.
CPC ............. *A61B 34/10* (2016.02); *A61B 5/0042* (2013.01); *A61B 5/055* (2013.01); *A61B 5/372* (2021.01);
(Continued)

(58) Field of Classification Search
CPC ....... A61B 5/4094; A61B 5/369; A61B 5/372; A61B 5/4064; A61B 5/384; A61B 5/0042; A61B 2034/105; A61B 2034/107
See application file for complete search history.

(56) References Cited

U.S. PATENT DOCUMENTS

2014/0222738 A1   8/2014  Joyce et al.
2018/0240549 A1   8/2018  Terry et al.
(Continued)

FOREIGN PATENT DOCUMENTS

JP   2014522283 A    9/2014
WO   2012170876 A2   12/2012
WO   2018015778 A1   1/2018

OTHER PUBLICATIONS

International Search Report and Written Opinion dated Jul. 31, 2020 in counterpart application No. PCT/EP2020/064759; in English (total 14 pages).
(Continued)

*Primary Examiner* — Gerald Johnson
(74) *Attorney, Agent, or Firm* — Seckel IP, PLLC

(57) ABSTRACT

The method of identifying a potentially surgically operable target zone in an epileptic patient's brain includes: providing a computerized platform modelling various zones of a primate brain and connectivity between said zones; providing a model of an epileptogenic zone and a model of the propagation of an epileptic discharge from an epileptic zone to a propagation zone; obtaining a patient's personalized computerized platform; deriving the potential target zones
(Continued)

Figure 1A:
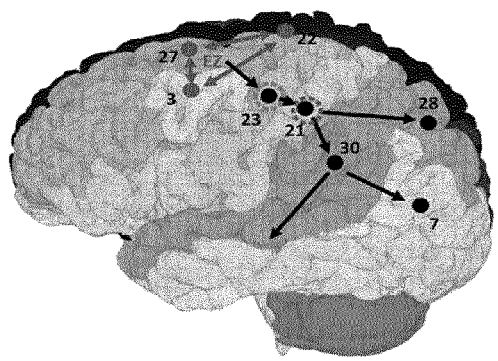
Figure 1B:
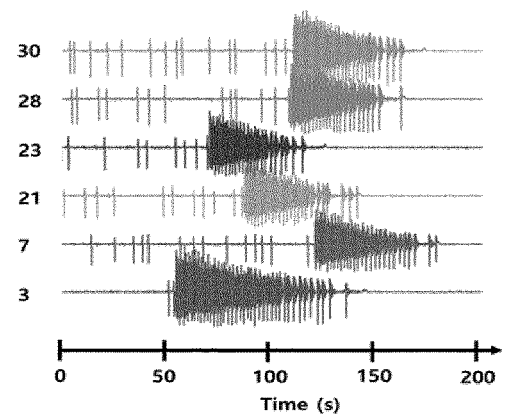
Figure 1C:
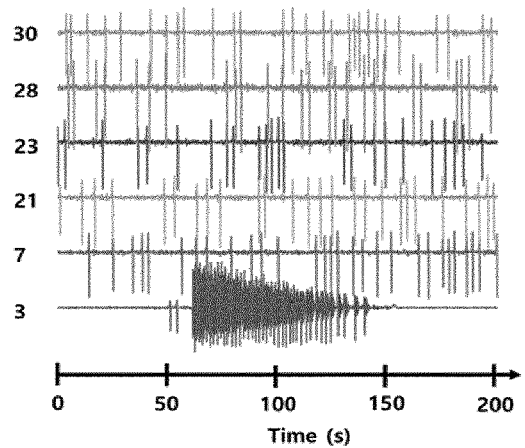
Figure 1D:
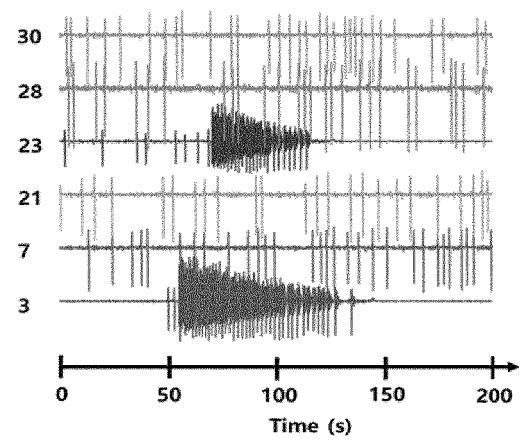

based on modularity analysis; evaluating the target zones' effectiveness by simulating epileptic seizures propagation in the personalized patient's computerized platform; evaluating the target zones' safety by simulating spatiotemporal brain activation patterns in a defined state condition and comparing the simulated spatiotemporal brain activation patterns obtained before removal of the target zone with the spatiotemporal brain activation patterns obtained after removal of the target zone; identifying the target zones which satisfy both effectiveness and safety evaluation criteria as potentially surgically operable target zones.

20 Claims, 9 Drawing Sheets

(51) Int. Cl.
  *A61B 5/055* (2006.01)
  *A61B 5/372* (2021.01)
  *A61B 5/384* (2021.01)

(52) U.S. Cl.
  CPC ............ *A61B 5/384* (2021.01); *A61B 5/4094* (2013.01); *A61B 2034/105* (2016.02); *A61B 2034/107* (2016.02); *A61B 2034/108* (2016.02)

(56) References Cited

U.S. PATENT DOCUMENTS

2019/0254585 A1    8/2019  Jirsa et al.
2020/0178832 A1*   6/2020  Berry ................... A61B 5/076

OTHER PUBLICATIONS

An et al., "Optimization of surgical intervention outside the epileptogenic zone in the Virtual Epileptic Patient (VEP)", PLOS Computational Biology, vol. 15, No. 6, Jun. 26, 2019 (Jun. 26, 2019), p. e100705-1 to 25 (total 25 pages) (in English; D2 cited in the ISR).

Rubinov et al., "Complex network measures of brain connectivity: Uses and interpretations", NeuroImage, Elsevier, Amsterdam, NL, vol. 52, No. 3, Sep. 1, 2010 (Sep. 1, 2010), pp. 1059-1069 (in English; D3 cited in the ISR).

Bansal et al., "Personalized brain network models for assessing structure-function relationships", arxiv.org, Cornell University Library, 201 Olin Library, Cornell University, Ithaca, NY 14853, Feb. 1, 2018 (Feb. 1, 2018), pp. 1-13 (in English; D4 cited in the ISR).

Olmi et al., "Controlling seizure propagation in large-scale brain networks", arxiv.org, Cornell University Library, 201 Olin Library, Cornell University, Ithaca, NY 14853, Apr. 10, 2018 (Apr. 10, 2018), pp. 1-25 (in English; D5 cited in the ISR).

Proix et al., "Individual brain structure and modelling predict seizure propagation", Brain, vol. 140, No. 3, Feb. 14, 2017 (Feb. 14, 2017), pp. 641-654 (in English; D6 cited in the ISR).

JP Office Action dated Oct. 24, 2023 in counterpart application No. JP 2021-570320; with English machine translation (total 6 pages) (note: WO2018015778, D1 cited in the JP Office Action dated Oct. 24, 2023 is not listed in this IDS since it was already listed in the IDS filed Nov. 26, 2021).

* cited by examiner

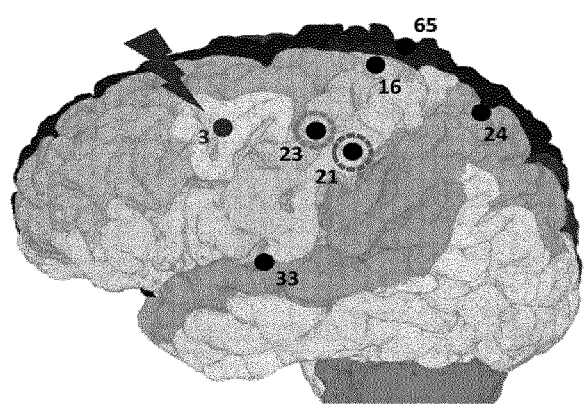
FIG. 1E
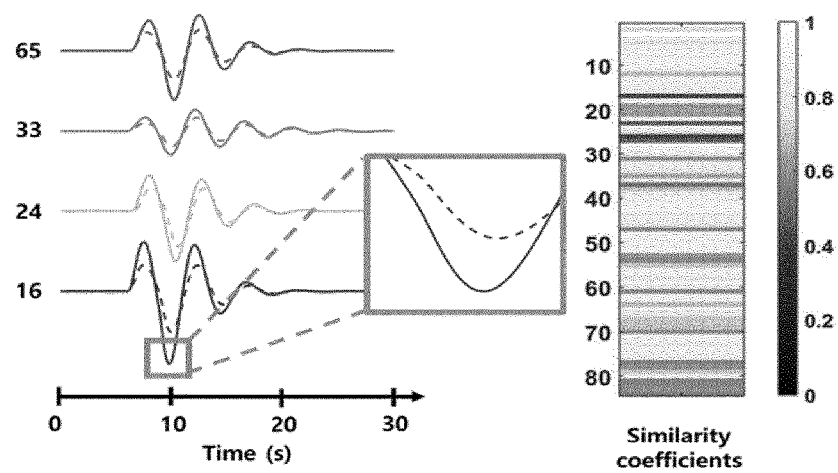
FIG. 1F
FIG. 1G
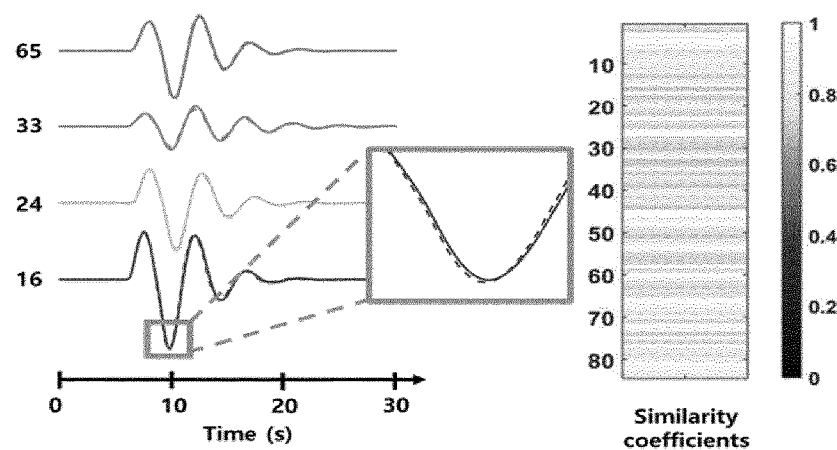

METHOD OF IDENTIFYING A SURGICALLY OPERABLE TARGET ZONE IN AN EPILEPTIC PATIENT'S BRAIN

The invention relates to a method of identifying a surgically operable target zone in an epileptic patient's brain.

Epilepsy is a chronic neurological disorder that is defined by the occurrence of repetitive unexpected seizures. The epileptic seizures, characterized as abnormal synchronization of neural activities, originate in a specific brain region and propagate to other regions through inter-regional structural interactions constituting the individual brain connectome, and produce various ictal symptoms depending on the recruited brain regions.

For the treatment of epilepsy, medication with antiepileptic drugs is preferentially applied, and surgical intervention is often offered as an option for drug-resistant patients, which account for more than 30% of patients. There are two main types of surgical strategies: resection and disconnection. Resection, which removes the brain regions generating seizures, results in seizure-free outcomes in 30-70% of the postoperative patients depending on the localization accuracy of epileptogenic zone (EZ) and the pathology of each patient. Disconnection, which severs nerve pathways that play an important role in seizure propagation, may have either a curative objective, i.e. an hemispherotomy, or may limit seizure propagation, i.e. a callosotomy. Although surgical intervention is generally accepted as an effective method to control drug-resistant seizures, only about 10% of patients might be considered candidates for surgery because EZs are often located in multiple brain regions simultaneously and involve eloquent areas, which are defined as brain regions where damage causes neurological complications such as language, memory and motor problems. Several alternative methods including multiple subpial transection, which could prevent neuronal synchronization in the EZ without altering normal functions by severing horizontal intracortical fibers while preserving vertical fibers in the eloquent cortex, have been tried for patients who are unsuitable for conventional surgery, but with variable results. Therefore, there is a clear need to provide more optimal surgical options for those patients. The alternative method should be 1) effective in seizure reduction, 2) able to provide flexible options depending on the inoperable EZ or technically inaccessible region for surgery, and 3) have minimal impact on normal brain functions.

Studies on epilepsy have mainly focused on investigation of the brain network dynamics of individual patients. By analyzing functional data, such as intracranial electrocorticographic (ECoG) signals and stereotactic electroencephalographic (SEEG) signals, many studies have examined network properties at each brain state including interictal, preictal, ictal, and postictal. In particular, network analysis based on graph theory has been able to not only identify characteristics of the seizure onset zone that would be targeted in resection surgery, but also observe changes in network topology over the onset and time-course of seizure. Several studies have shown that one large regular network is formed at seizure onset compared to the network in the interictal period, which consists of several small sub-networks. These results suggest that seizures may be prevented by disrupting the formation of large regular networks through the disconnection of well-chosen sub-networks. Furthermore, several other studies have demonstrated that the epileptic brain network has more segregated features than healthy brain network. Meanwhile, by analyzing structural data based on Magnetic Resonance Imaging (MRI), many studies have reported structural abnormalities in the epileptic brain distinct from the normal brain, which include not only regional alterations, but also abnormalities in white matter tracts, i.e. in the inter-regional connectivity. From the network perspective, several studies have shown an increase of local network connectivity and a decrease of global network connectivity in the epileptic brain, even though the situation is more complex depending on whether brain regions are involved in seizures generation and propagation. It was further reported that the healthy brain network present widespread distribution of hub regions, while the epileptic brain network has hub regions concentrated in specific areas, for example, in temporal lobe epilepsy, paralimbic/limbic and temporal association cortices. The results of these studies suggest that the epileptic brain comprises a distinct modular structure and that seizure propagation can be controlled by blocking interactions between the modules, i.e. by severing the connections.

Translation of any computational modeling approach require the personalization of the brain network models, tailored to a patient's connectivity and lesion. Personalized brain network models, based on brain connectome and clinical information from each patient, have been able to simulate individual seizure propagation patterns.

At present, efforts in the field focus on improving the localization of EZ and develop strategies to effectively remove the identified zone.

Accordingly, a need exists for methods that are allowing the identification of minimally invasive surgical interventions, particularly applicable for case in which the EZ is non-operable.

In accordance with a first aspect, the invention concerns a method of identifying a potentially surgically operable target zone in an epileptic patient's brain comprising the following steps:

providing a computerized platform modelling various zones of a primate brain and connectivity between said zones;

providing a model of an epileptogenic zone and a model of the propagation of an epileptic discharge from an epileptic zone to a propagation zone, the model of the epileptogenic zone being a mathematical model describing the onset, the time-course and the offset of the epileptic discharge, and loading said models in the computerized platform to obtain a computerized platform modelling an epileptic primate brain;

identifying an estimated epileptogenic zone in the patient's brain;

personalizing the computerized platform modelling the epileptic primate brain according to the patient's brain structural connectivity and parametrizing the estimated epileptogenic zone, in said computerized platform, as an epileptogenic zone, to obtain a patient's personalized computerized platform;

carrying out a modularity analysis with the patient's brain structural connectivity to derive the potential target zones acting as hubs in the interaction between modules, said potential target zones being outside the potential epileptogenic zone and such as, if they are surgically opered or removed, are minimizing epileptic seizure propagation, and evaluating the potential target zones' effectiveness to minimize propagation of epileptic seizures by network simulation simulating propagation characteristics of said epileptic seizures in the personalized patient's computerized platform and identifying one or more effective target zones, said effective target zones being outside the epileptogenic zone and such as, if they are surgically operated, are minimizing seizure propagation;

evaluating the potential target zones' safety to maintain normal brain functions by network simulation wherein simulated spatiotemporal brain activation patterns in a defined state condition are obtained from the personalized computerized platform before and after removal of said zone and these simulated spatiotemporal brain activation patterns obtained before removal of the zone are compared with the simulated spatiotemporal brain activation patterns obtained after removal of the zone and, if the spatiotemporal brain activation patterns obtained before removal of the zone are substantially the same as the spatiotemporal brain activation patterns obtained after removal of the zone, then identifying said potential target zone as a safe target zone; and identifying or suggesting the potential target zones which satisfy both effectiveness and safety evaluation as potentially surgically operable target zones.

Preferentially, —the epileptogenic zone in the patient's brain is estimated clinically; —the target zones are nodes or edges involved in the epileptic seizure propagation said nodes and edges corresponding to brain regions and fiber tracts between brain regions, respectively; —the structural brain connectivity is reconstructed from images data of the patient brain acquired using magnetic resonance imaging, diffusion-weighted magnetic resonance imaging, nuclear magnetic resonance imaging and/or magnetic resonance tomography; —the computerized platform modelling the epileptic primate brain is personalized according to the patient-specific brain connectivity and the functional data of the patient; —the functional data are acquired through electroencephalography (EEG) or stereotactic EEG (SEEG) techniques; —the modularity analysis is carried out to derive the potential target zone; —for the implementation of the modularity analysis, a constraint is added in order to prevent inoperable nodes from being derived as target zones; —systematic simulations are carried out in the patient's personalized computerized platform, wherein if an identified target zone does not satisfy the evaluation criteria, a new target zone is derived by feeding back the simulation results to the analysis again; —the defined state condition is the resting state condition; —a plurality of resting states conditions are used for simulation; and—the modularity analysis provides a non-overlapping modular structure that minimizes edges between modules and maximizes edges within modules.

Hence, focusing on the fact that the epileptic brain network has distinct segregation characteristics, the present invention employs modularity analysis with structural brain connectivity from each patient, in order to derive brain regions and fiber tracts as target zones (TZs) that should be removed for resection and disconnection surgery, respectively. It is assumed the worst-case scenario in which the EZ is an inoperable zone, so that the proposed in silico surgical approach induces seizure relief by suppressing seizure propagation to other brain areas even though it cannot prevent seizure generation in EZs. Reducing the involvement of propagation networks is a major factor to reduce the impact of seizures, particularly the loss of consciousness. The acquired TZs are evaluated by personalized brain network simulations in terms of the effectiveness to control seizure propagation and the safety to maintain normal brain functions, and then optimized according to the results.

Other features and aspects of the present invention will be apparent from the following description and the accompanying drawings, in which:

FIG. 1A to 1G illustrate the brain simulations carried out according to the method of the invention using The Virtual Brain. FIGS. 1A to 1D show network simulations for the effectiveness evaluation. The brain network model assesses the effectiveness by identifying the seizure propagation characteristics. Those figures show simulated signals at each brain node before (FIG. 1B) and after (FIGS. 1C and 1D) removal of the node 23 or node 21 respectively, when nodes 3, 22 and 27 act as epileptogenic zone. FIGS. 1E to 1G show network simulations for the safety evaluation. The brain network model assesses the safety by investigating the integrity of the transient spatiotemporal trajectory following electrical stimulation at certain nodes. When a stimulus is applied to the node 3, the stimulation induces different response signals at each node (solid lines, FIGS. 1F and 1G). When removing all connections from the node 23, the response signals (dotted lines, FIG. 1F) at each node are altered compared to before removal. On the other hand, when eliminating the node 21, the response signals (dotted lines, FIG. 1G) are not significantly different from that before removal. The color bars represent similarity coefficients between the response signals at each node before and after elimination.

Figure 2A:
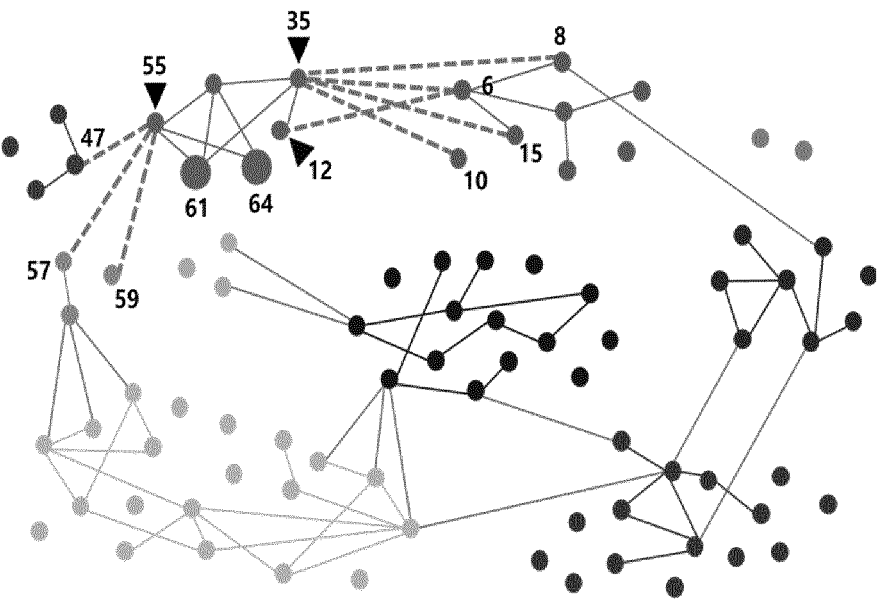
Figure 2B:
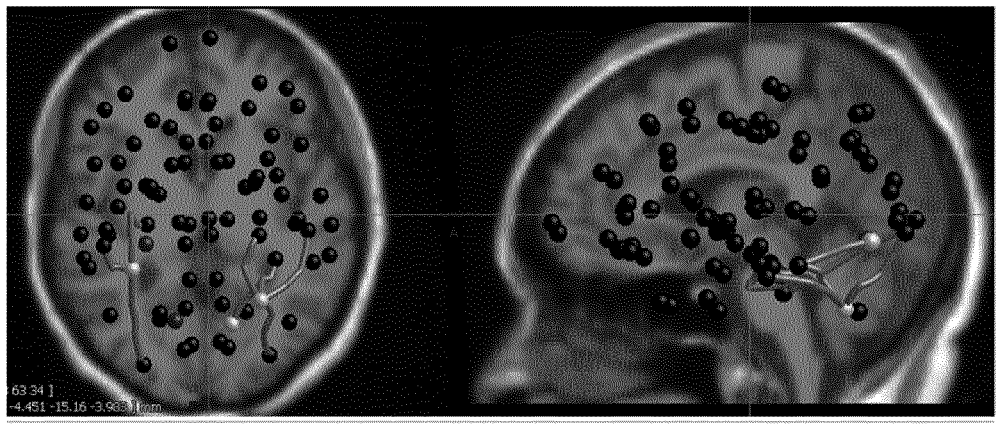
Figure 2C:
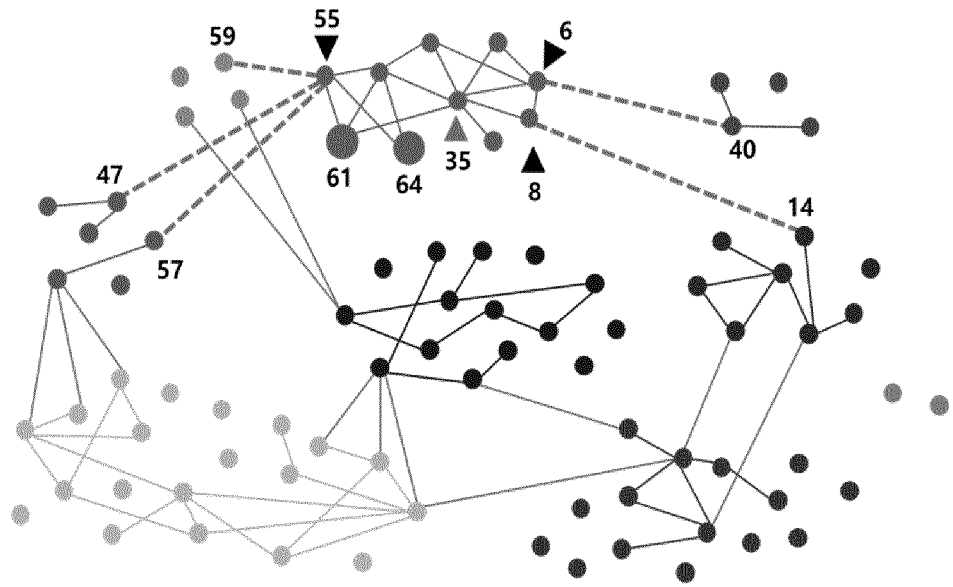
Figure 2D:
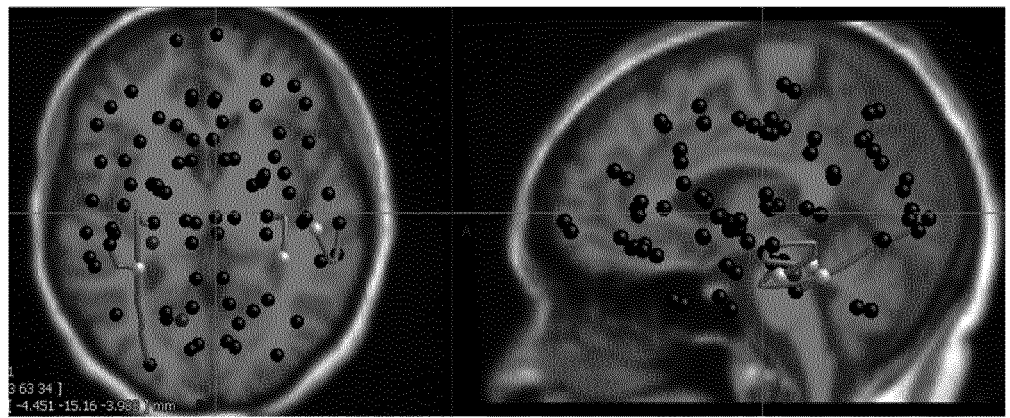

FIGS. 2A to 2D illustrate the target zones that are derived from the modularity analysis for a particular patient according to the method of the invention. FIG. 2A shows a modular structure when setting the epileptogenic zones to inoperable zones with a resolution parameter of 1.25. The brain network is divided into seven modules and the EZ sub-module (upper module in the Figure) is subdivided into four sub-modules, so that each EZ (nodes 61 and 64, large circles) and its neighboring nodes belong to the same sub-module. Based on this modular structure, three nodes (black triangles) and eight edges (gray dotted lines) are derived as target nodes and target edges respectively. For the visualization, only the edges with a connection weight greater than 0.08 are drawn. FIG. 2B shows anatomical locations and lists of the acquired target zones. Middle gray nodes represent the epileptogenic zones, light gray nodes and gray edges indicate target nodes and target edges. FIG. 2C shows modular structure when adding the critical node (gray triangle) to inoperable zone in modularity analysis with a resolution parameter of 1.25. The brain network is divided into 8 modules and the epileptogenic zone sub-module (upper module) is subdivided into two sub-modules, so that each inoperable zone and its neighboring nodes belong to the same sub-module. Based on this modular structure, 3 nodes (black triangles) and five edges (gray dotted lines) are derived as new target nodes and target edges respectively. FIG. 2D shows anatomical locations and list of the newly obtained target zones. Middle gray nodes represent epileptogenic zones, light gray nodes and green edges indicate target nodes and target edges.

Figure 3A:
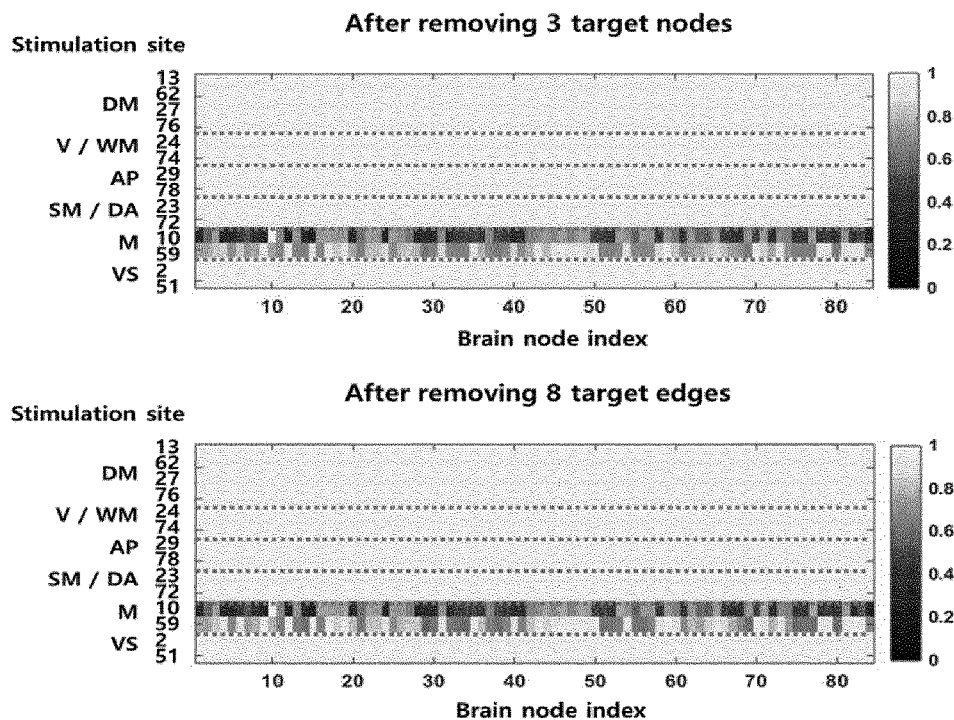
Figure 3B:
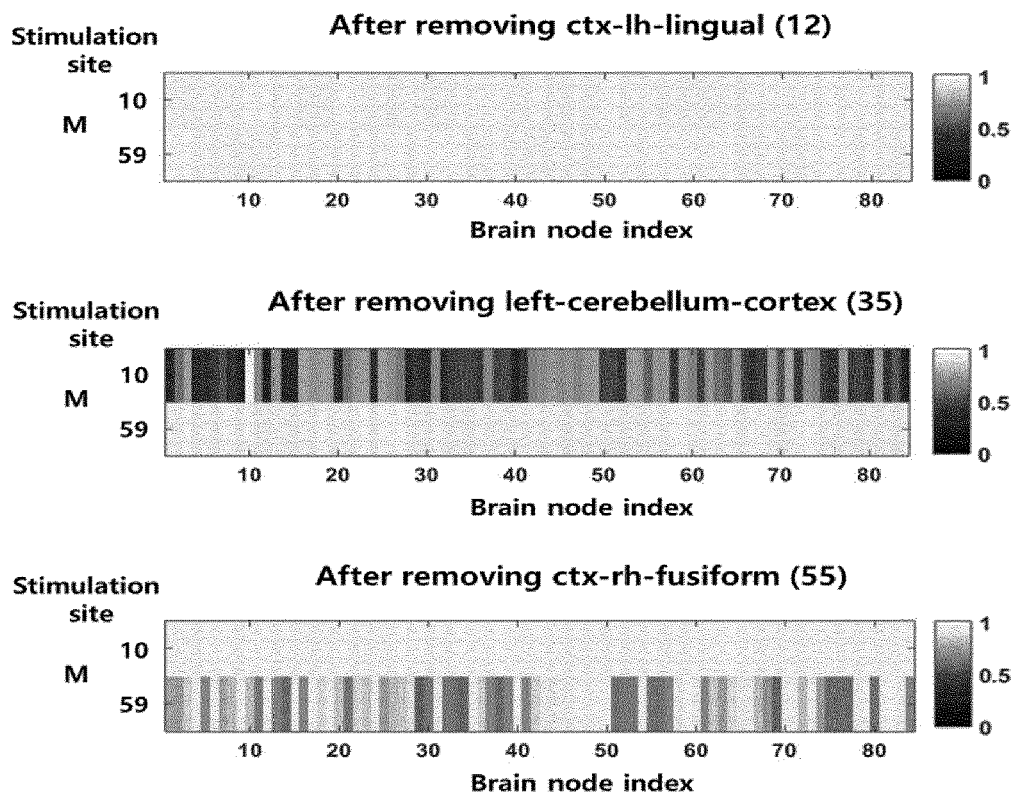

FIGS. 3A and 3B illustrate the safety evaluation of the target zones according to the method of the invention. FIG. 3A shows the network simulation results for safety assessment. When stimulation is applied to the brain nodes that can reproduce each resting state network, the difference between response signals before and after removing target zones are presented as the similarity coefficient. The similarity coefficient is calculated independently in all brain nodes, and the shades of gray of the figure are indicative of the values of the similarity coefficient. FIG. 3B illustrates the identification of the critical node. When each node belonging to the initially obtained target nodes is eliminated, the degree of alteration of the response network, corresponding to the memory network M, is represented as the similarity coefficient.

Figure 4A:
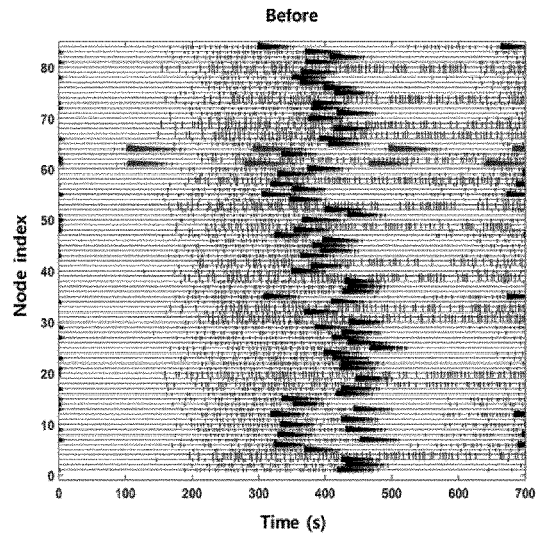
Figure 4B:
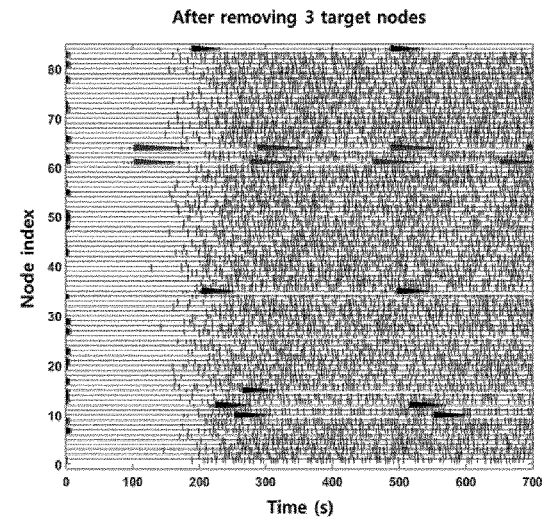
Figure 4C:
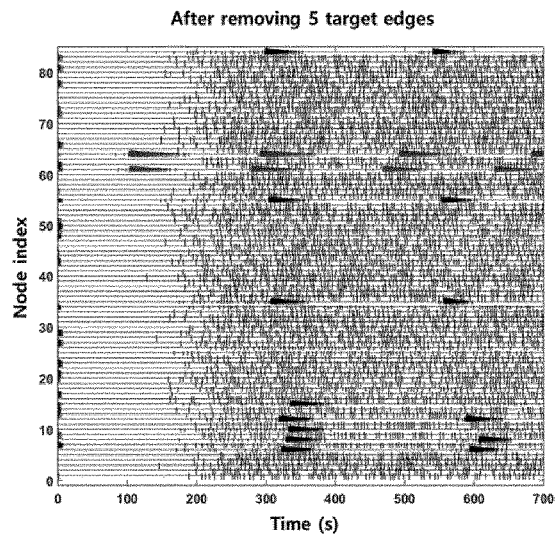
Figure 4D:
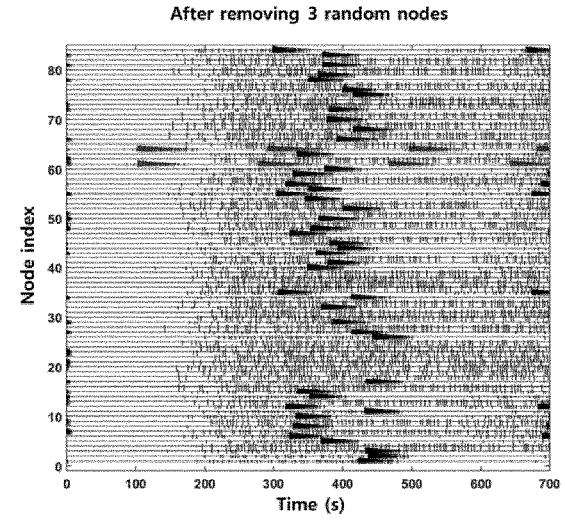

FIGS. 4A to 4D illustrate the network simulation results for effectiveness verification according to the method of the invention, and local field potentials in all brain nodes. They further illustrate the propagation characteristics of the seizure occurred from EZs (node 61 and 64). The results shown in FIG. 4A are those obtained before removing the target zones, the results shown in FIG. 4B are obtained after removing 3 target nodes, those shown in FIG. 4C are obtained after removing 5 target edges, and those shown in FIG. 4D are obtained after removing 3 random nodes.

Figure 5A:
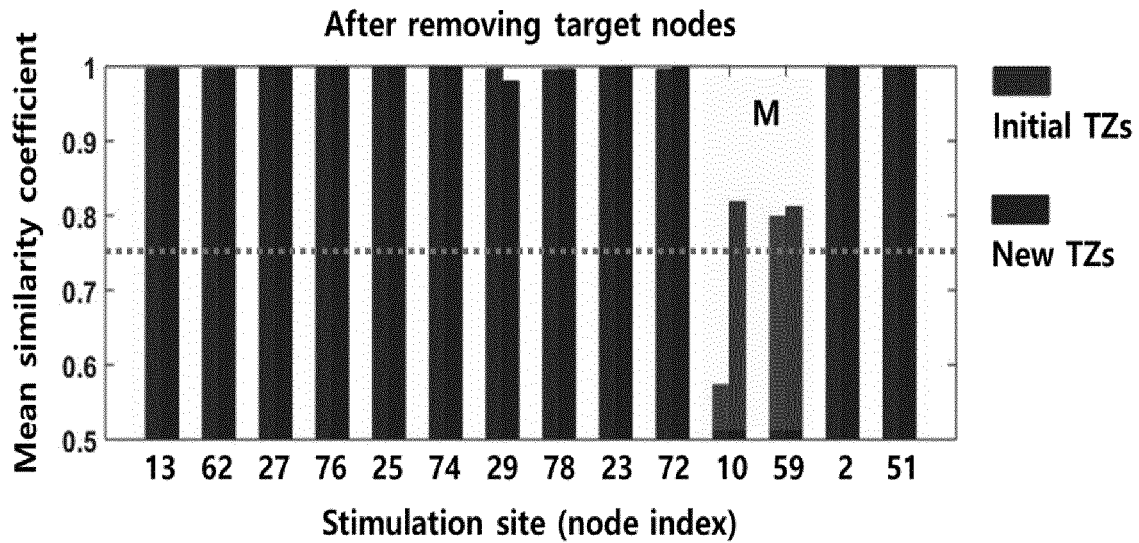
Figure 5B:
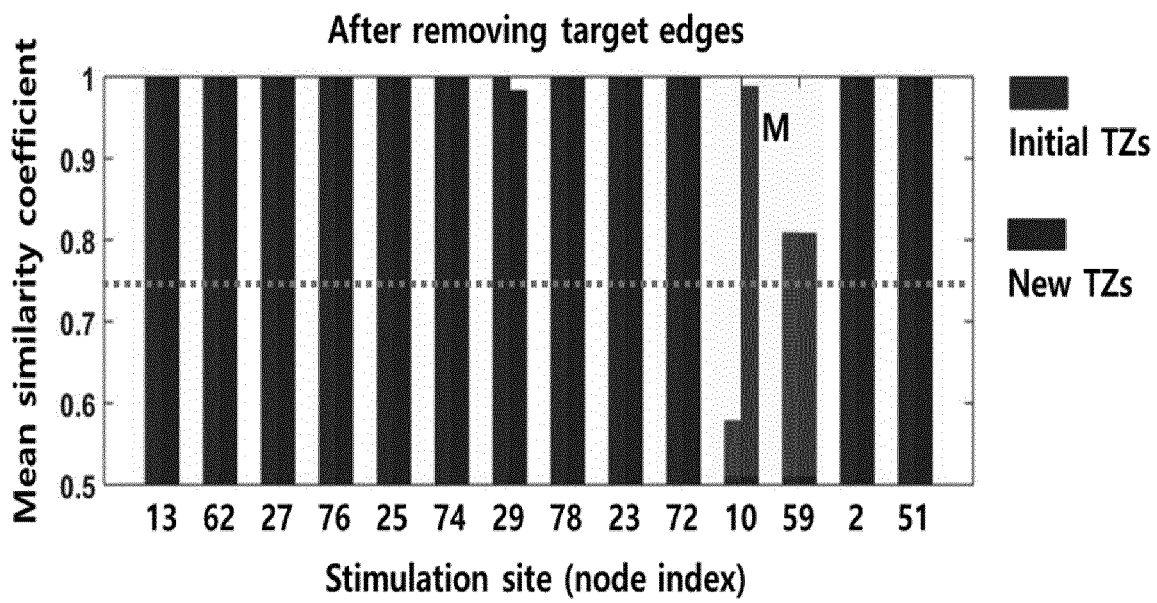

FIGS. 5A and 5B illustrate the safety evaluation results for the initial target zones and the new target zones obtained by the feedback according to the method of the invention. The histogram shows the mean value of the similarity coefficients between the responsive activation patterns due to stimulation in all brain regions, before and after removal of the target nodes and target edges, respectively. While the elimination of initial TZs has a value lower than threshold (0.75) when stimulation is applied to node 10 to reproduce memory network (M), the removal of new TZs has values higher than the threshold in all stimulation sites.

Figure 6A:
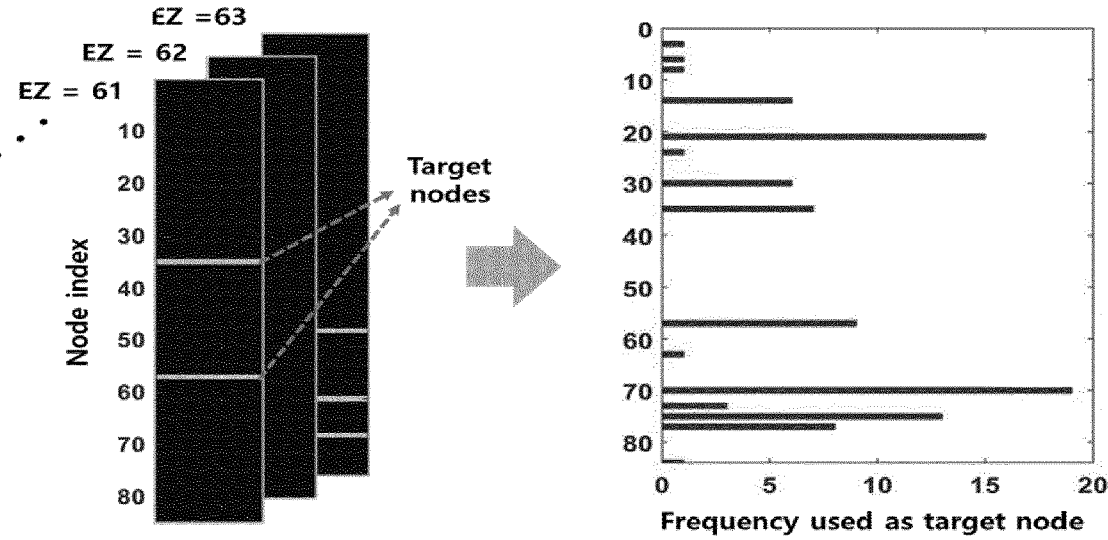
Figure 6B:
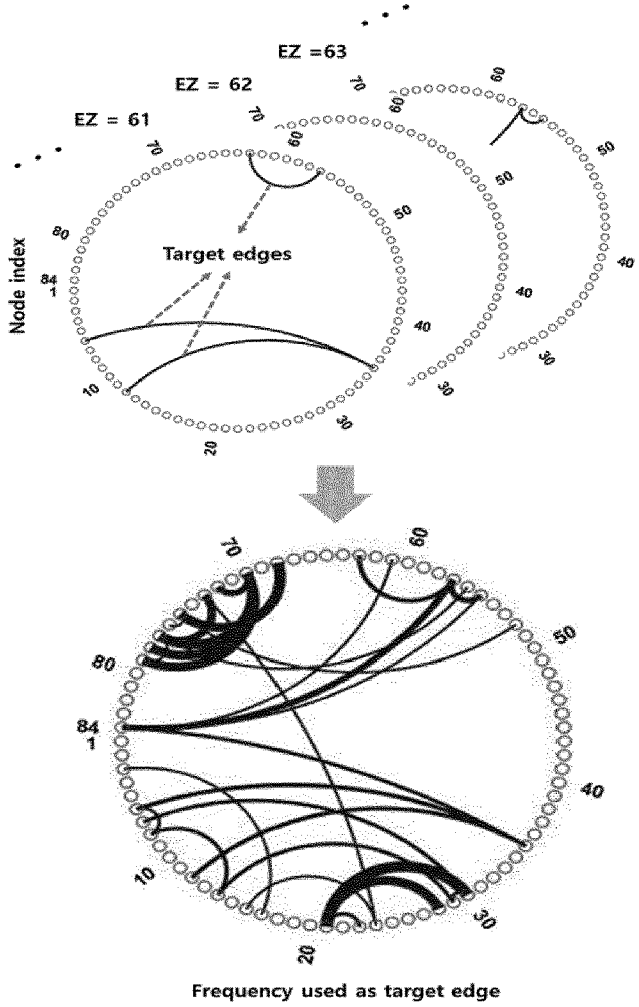
Figure 6C:
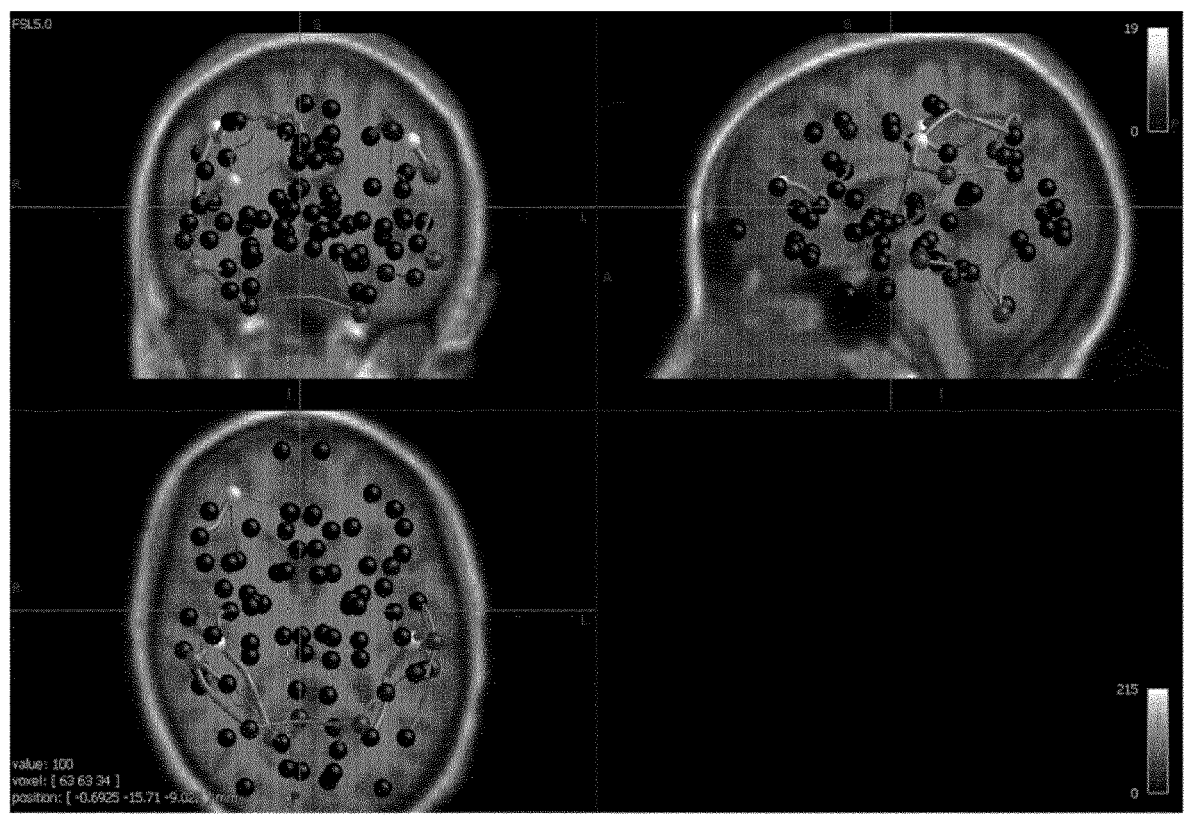

FIGS. 6A to 6C illustrates that the target zones depend on the location of the epileptogenic zones. FIG. 6A shows target nodes according to the location of the epileptogenic zone and their cumulative results. Gray horizontal bars in each column indicate the target nodes, when the epileptogenic zone is located in each different node. FIG. 6B shows target edges according to the location of epileptogenic zone and their cumulative results. Connection lines between the nodes in each slice indicate the target edges, when the epileptogenic zone is located in each different node. The cumulative result identifies several nodes and edges frequently used as target zone. Here, the resolution parameter for the modularity analysis is set to 1.0. FIG. 6C shows anatomical locations of the nodes and the edges frequently obtained as target zones. The shade of gray of used for the nodes and the thickness of edges indicate the frequency used as target zone.

The invention concerns a method of identifying a surgically operable target zone in an epileptic brain of a primate epileptic patient. The patients are, in particular, human patients, which are drug-resistant epileptic patients. The method according to the invention constitutes an in-silico surgical approach that is based on the graph theoretical analysis using patient-specific brain connectome, specifically modularity analysis, and personalized brain network simulations, and which suggests effective and safe intervention options by minimizing the impact on the brain's signal transmission capacity.

The method according to the invention comprises a step according to which a computerized platform, i.e. a brain network, modelling various zones of a primate brain and connectivity between said zones is provided. Such a computerized platform constitutes a virtual brain. An example of a virtual brain is disclosed in the publication document entitled "*The Virtual Brain: a simulator of primate brain network dynamics*", Paula Sanz Leon et al., 11 Jun. 2013, which is incorporated herein, by citation of reference. In this document, the virtual brain is disclosed as a neuro-informatics platform for full brain network simulations using biologically realistic connectivity.

This simulation environment enables the model-based inference of neurophysiological mechanisms across different brain scales that underlie the generation of macroscopic neuroimaging signals including functional Magnetic Resonance Imaging (fMRI), EEG and Magnetoencephalography (MEG). It allows the reproduction and evaluation of personalized configurations of the brain by using individual subject data.

According to a further step of the invention, a model of an epileptogenic zone (EZ) and a model of the propagation of an epileptic discharge from an epileptic zone to a propagation zone (PZ) are provided. These models are then loaded in the computerized platform in order to obtain a computerized platform modelling an epileptic primate brain.

The model of the EZ is a mathematical model describing the onset, the time-course and the offset of the epileptic discharge. Such a model is disclosed, for example, in the publication document entitled "*On the nature of seizure dynamics*", Jirsa et al., Brain 2014, 137, 2210-2230, which is incorporated herein, by citation of reference. This model is named Epileptor.

The model of the PZ is identical to the one of an EZ, however with an excitability parameter inferior to the critical value $x_{0C}=-2.05$. All other brain areas may be modelled by Epileptors with excitability values far from the threshold, or equivalently standard neural population models as disclosed in Paula Sanz Leon et al., 11 Jun. 2013, which is incorporated herein, by citation of reference. The coupling between brain areas follows a mathematical model as disclosed in the publication document entitled "*Permittivity Coupling across Brain Regions Determines Seizure Recruitment in Partial Epilepsy*", Timothée Proix et al., The Journal of Neuroscience, Nov. 5, 2014, 34(45):15009-15021, which is incorporated herein, by citation of reference.

According to a further step of the invention, structural and functional data of the brain of the epileptic patient are acquired. Brain connectome is reconstructed from the structural data, and epileptogenic zone is estimated from the functional data.

The structural data are, for example, images data of the patient brain acquired using magnetic resonance imaging (MRI), diffusion-weighted magnetic resonance imaging (DW-MRI), nuclear magnetic resonance imaging (NMRI), or magnetic resonance tomography (MRT). Functional data are for example EEG or SEEG signals. A estimate of the epileptogenic zone may be clinical, or may be provided using a non-clinical method, as the method disclosed in the international application published under the number WO2018/015779.

According to a further step of the invention, the computerized platform modelling the epileptic primate brain is personalized according to the patient's brain structural connectivity. The estimated epileptogenic zone is further parametrized in said computerized platform, as an epileptogenic zone, to obtain a patient's personalized computerized platform, i.e. a personalized brain network.

According to a further step of the invention, potential target zone is derived based on modularity analysis and the effectiveness of the target zone is evaluated by network simulation. The propagation characteristics of epileptic seizures are simulated in the personalized patient's computerized platform and one or more effective target zones are identified. The effective target zones are outside the epileptogenic zone. Additionally, they are such as, if they are surgically operated on or removed, they are minimizing seizure propagation.

According to a further step of the invention, the safety of the potential target zone is evaluated by network simulation. Simulated spatiotemporal brain activation patterns in a defined state condition are obtained from the personalized computerized platform before and after removal of said zone. This defined state condition is, for example, the resting state condition. However, this may be other state conditions, for example, a state condition wherein the brain is under a memorization mode, a state wherein the brain is under a mode of perceiving things, or a state wherein the brain is under an attention mode. According to a further step of the invention, the simulated spatiotemporal brain activation patterns obtained before removal of the target zone are compared with the spatiotemporal brain activation patterns obtained after removal of the zone. If the spatiotemporal brain activation patterns obtained before removal of the zone are substantially the same as the spatiotemporal brain activation patterns obtained after removal of the zone, then said potential target zone is identified as a safe target zone.

According to a further step of the invention, the potential target zones that satisfy both effectiveness and safety evaluation criteria are suggested as a surgically operable target zone. To evaluate the effectiveness and safety of the identified TZ, brain network simulations are employed. Based on the patient-specific network model constructed by structural brain connectivity and estimation for EZs of each patient, the effectiveness of the TZs are assessed by simulating seizure propagation characteristics before and after removal of the TZs. Reducing the involvement of propagation networks is a major factor to reduce the impact of seizures, particularly the loss of consciousness. Loss of consciousness is one of the major signs and is clearly linked to the synchronization in propagation network, particularly fronto-parietal networks during temporal lobe epilepsy seizures. It is recognized that a good outcome after epilepsy surgery may include patients with residual subjective symptoms (aura) but without any more objective signs (automatism, loss of consciousness).

According to the method of the invention, modularity analysis is generally used to investigate synchronization characteristics between brain regions. Each patient's brain network has a distinct modular structure. From the patient-specific modular structure, nodes and edges connecting the EZ sub-module with other submodules or modules are extracted as surgical options, TZs, to suppress seizure propagation in a patient-specific manner. By adding a constraint to the existing modularity analysis, flexible TZs excluding inoperable zones are derived, which may provide alternative surgical methods that can result in seizure relief to patients who are considered unsuitable for the conventional surgery since resection of EZ may cause severe neurological complications. Moreover, the parameter sweep in the modularity analysis obtained different modular structures, ultimately resulted in multiple TZ options. This multiplicity is crucial in that clinicians can select the surgical target within multiple options, taking into account the number of interventions and the suppression degree of seizures. The clinicians can also consider not only the specific regions that should be excluded for surgery based on their clinical experiences but also the technically challenging regions.

Based on the patient-specific modular structure obtained from the structural brain connectivity and estimation, in particular a clinical estimation, for the EZ of a patient, brain regions and fiber tracts acting as hubs in the interaction between the modules, i.e. connecting different modules, are identified as TZs for surgical intervention. The acquired TZs are evaluated through personalized brain network simulations regarding their effectiveness and safety.

Practically, the results contain several TZ variants that are appropriate each patient's circumstance considering the location of EZ and individual brain connectome. The final TZ variants are effective surgical targets preventing seizure propagation with maintaining normal brain functions.

The systematic simulations allow to identify different TZs according to the locations of EZ. The results can be used not only to identify major nodes and edges involved in seizure propagation, but also as a reference to elicit reasonable surgical targets if there are several clinical hypotheses for the EZ location.

Since the effect on seizure reduction is highly dependent on the location or contribution of each node in the network, a systematic approach is carried out according to the invention to identify the target node. Furthermore, network effects are investigated at a whole-brain scale. In particular, the derived TZs are based on the clinical estimation and brain connectivity analysis of each patient, and examined the effect of TZ removal in the seizure propagation network through personalized brain network simulation based on individual brain connectome.

Critical to surgical intervention outside of the EZ is the investigation of the safety of the procedure according to the invention. Safety is operationalized by the concept of preservation of signal transmission properties of the brain network, assuming those to be directly linked to the brain function. The brain function capacity is advantageously, at least implicitly, quantified by functional connectivity of the resting state (RS). This attempts to quantify, by construction, properties of attractor states at rest. The TZs are evaluated by distinctly quantifying the changes in network characteristics at resting state in pre- and post-surgical condition. Perturbations to attractor states allow to sample additional properties of the brain network such as attractor stability, convergence and divergence of flows, and thus significantly enhance the characterization of its dynamic properties. Stimulation is a reliable way to induce perturbation to each state, which generates a spatiotemporal response pattern according to the stimulation location and brain connectivity. Stimulation is employed to reproduce each RS network and to clearly quantify the changes in the network properties before and after eliminating the TZs. To best estimate the transient spatiotemporal trajectory due to stimulation applied to individual brain regions, spatial and temporal properties before and after eliminating the TZs are compared. Hence, transient trajectories are highly constrained by the structural properties of the network and show a surprisingly low-dimensional behavior, after an initial local stimulation artifact. These transient trajectory properties are exploited to quantify the difference of response network due to stimulation, and assumed that the changes in the response pattern after removal of TZ indicate a negative impact in terms of brain functionality, i.e. the removal of the TZ is interpreted as unsafe if the difference in response patterns before and after removal of the TZ is large.

FIG. 1 illustrates an example for the target zone evaluation. As shown in FIGS. 1A to 1D, effectiveness to control seizure propagation is assessed by the degree of seizure propagation suppression. FIG. 1B illustrates simulated signals at several brain nodes identified in FIG. 1A, when nodes 3 (ctx-lh-caudalmiddlefrontal), 22 (ctx-lh-posteriorcingulate) and 27 (ctx-lh-superiorfrontal) are EZs. It appears that the nodes are seizure-recruited following some delays depending on connectivity between nodes, after the seizure is generated from the EZs. On the other hand, after removing a specific node in the seizure propagation pathway, i.e. the node 23 (ctx-lh-precentral) or the node 21 (ctx-lh-postcentral), the simulated brain signals show that the propagation beyond each node is prevented even if the seizure is still occurred from the EZs. This is shown in FIGS. 1C and 1D.

In this way, the characteristics of seizure propagation are observed after eliminating target nodes or target edges for effectiveness evaluation of the TZ.

The evaluation of safety of the intervention rests on the maximization of the signal transmission properties of the brain network. The latter is assessed by stimulating relevant brain regions and quantifying the subsequent transient trajectory of brain network activation. More specifically, safety is evaluated by assessing similarity of the spatiotemporal brain activation patterns following electrical stimulation, before and after removal of the TZ. To investigate the variations in resting state (RS) networks, the brain regions where the stimulation is applied can reproduce similar responsive networks to each of the eight well-known RS network.

FIGS. 1E to 1G illustrate an example of the response network when a stimulus is applied to a specific node: the node 3. The stimulation locally activates the stimulated node first, followed by a propagation and sequential recruitment through the connectome, thereby generating a unique spatiotemporal response pattern specific to the stimulation site. The solid lines and dotted lines show the simulated signals obtained from several brain nodes before and after eliminating a particular node: the node 23 in FIG. 1F, and the node 21 in FIG. 1G. Compared with the pre-removal response pattern, the response signals are altered following the removal of node 23, whereas the response signals appear unaffected following the removal of node 21. The bars represent the degree of these differences quantitatively, i.e., as similarity coefficients. These results illustrate the sensitivity of the spatiotemporal seizure organization to network alterations. In this way, the safety of TZ is evaluated by systematically stimulating specific nodes, which reproduce each RS network, and comparing the response patterns before and after eliminating target nodes or target edges. If the TZ is judged to be inadequate based on the network simulation results, another TZ is derived by applying the results to the modularity analysis again. Through this feedback approach, the optimized TZ that effectively prevents seizure propagation while minimally affecting normal brain functions can be obtained.

Finally, the method according to the invention proposes a personalized in-silico surgical approach able to suggest effective and safe surgical options for each epilepsy patient. It focuses in particular on deriving effective alternative methods for those cases where EZs are inoperable because of issues related with neurological complications. Based preferentially on modularity analysis using structural brain connectivity from each patient, TZs that are considered as surgical sites are obtained. The acquired TZs are evaluated by personalized brain network simulations in terms of effectiveness and safety. Through the feedback approach combining modularity analysis and brain network simulations, the optimized TZ options that minimize seizure propagation while not affecting normal brain functions are obtained. It demonstrates the possibility of computational neuroscience field being able to construct a paradigm for personalized medicine by deriving innovative surgical options suitable for each patient and predicting the surgical outcomes.

Example 1: Materials and Methods

The method according to the invention is advantageously based on graph theoretical analysis and brain network simulations. Preferentially, from the modularity analysis considering inoperable zones, brain regions and fiber tracts acting as hubs in the interaction between the modules are derived as TZs. Then, the obtained TZs are evaluated in terms of the effectiveness and the safety by personalized brain network simulations using The Virtual Brain (TVB), a platform to simulate the brain network dynamics. If the TZ does not satisfy the evaluation criteria, a new TZ is derived by feeding back the simulation results to the modularity analysis again. Through the feedback approach, the optimized TZ options, that minimize seizure propagation while not affecting normal brain functions, is obtained.

Structural Brain Network Reconstruction

Neuroimaging data are obtained from 7 drug-resistant epilepsy patients. The patients have EZs with different locations and underwent comprehensive presurgical evaluations. The structural brain network of each patient is reconstructed from diffusion MRI scans and T1-weighted images (Siemens Magnetom Verio™ 3T MRscanner) using the SCRIPTS™ pipeline. Each patient's brain is divided into 84 regions, which include 68 cortical regions based on the Desikan-Killiany atlas, and 16 subcortical regions. Connection strengths between the brain regions are defined based on the number of streamlines, which are fiber tracts, and tract lengths to determine signal transmission delays between the regions are also derived.

Target Zone Derivation Based on the Patient Specific Modular Structure

To analyze the modular structure of the brain network, a Matlab toolbox is used. The modularity analysis, that is based on Newman's spectral algorithm, provides the non-overlapping modular structure that minimizes edges between modules and maximizes edges within modules. However, other toolboxes, that may be based on the Newman's spectral algorithm, or on other algorithms, may be used for the modularity analysis. For example, such another toolbox, which is a Matlab toolbox, is disclosed in the document NeuroImage, Vol. 52, Issue 3, September 2010, p. 1059-1069, entitled Complex network measures of brain connectivity, uses and interpretations, Mikail Rubinov et al. Modularity analysis that was carried out with the Matlab toolbox based on the Newman's algorithm allows to compute the leading eigen vector of the modularity matrix B of the equation hereunder and divides the network nodes into 2 modules according to the signs of the elements in the eigen vector.

$$B_{ij} = \left(A_{ij} - \alpha \frac{k_i k_j}{2m}\right), Q = \frac{1}{4m} \Sigma_{ij} B_{ij} s_i s_j$$

In this equation, $A_{ij}$ represents a weight value between the node i and the node j, $k_i$ and $k_j$ indicate the degree of each node, m denotes the total number of edges in the network. $\alpha$ is a resolution parameter for the analysis, the classic value is 1. The division is fine-tuned by the node moving method to obtain maximal modularity coefficient Q. The modularity coefficient has a value ranging from 0 to 1, the value of 0.3 or higher generally indicating a good division. $s_i$ and $s_j$ represent group membership variables that have a value of +1 or −1 depending on the group to which each node belongs. Each module, which is divided based on the eigen vector algorithm, is further divided into 2 modules until there is no effective division that results in a positive modularity coefficient. A constraint is added to the existing toolbox in order to prevent inoperable nodes from being derived as TZ. First, the group membership variable values of the nodes classified by the eigenvector algorithm are identified. Then, if the inoperable node and its neighboring nodes, i.e. the adjacent nodes based on the weight matrix, do not have the same value, it sets the values of them to the value that most of them have. In other words, the constraint limits the inoperable node and its neighbor nodes to belong to the same module, so that the inoperable node does not act as a hub connecting the modules. Meanwhile, the resolution parameter α is swept from 0.5 to 1.5 with intervals of 0.25 to obtain multiple modular structures. The resolution parameter determines the size of each module, i.e., the number of modules, in dividing the network nodes into modules. A high parameter value derives a modular structure consisting of small modules, i.e. the large number of modules, and a low parameter value obtains a structure consisting of large modules, i.e. the small number of modules.

To derive the target zones from the modularity analysis, the EZs and inoperable zones are preferentially set first. The EZs are fixed according to the clinical evaluation of each patient, and the inoperable zones are arbitrarily set to all EZs, i.e. it is assumed the worst-case scenario in which all EZs cannot be surgically removed. In fact, it is wanted to obtain TZs excluding all EZs for resection surgery and excluding all fiber tracts connected to the EZs for disconnection surgery. The strategy to suppress the seizure propagation is to divide each patient's brain network into multiple modules and then remove the connections, i.e. the nodes or edges, from the module containing the EZ module to the other modules. However, in the modularity analysis, when a low resolution parameter is used, a relatively large number of nodes may belong to the same module with EZ, and possibly, still quite a few nodes may be seizure-recruited even if the TZs are eliminated. To control this issue, i.e. to prevent a significant number of nodes from becoming seizure-remained nodes, it is chosen to divide EZ module to sub-modules once again and to define the TZs as the nodes/edges that connect the submodule including the EZ submodule to other submodules or modules. The nodes and the edges acquired for resection and disconnection surgery are named as target nodes and target edges, respectively. Since the resolution parameter is controlled in the modularity analysis in both division processes, multiple modular structures are obtained for the same patient, thereby it could provide multiple intervention options for target nodes and target edges. All of the procedures described above are automatically performed by the Matlab model that is developed. The model could yield multiple TZ options according to the location of EZ and inoperable zone.

Brain Network Simulation Using the Virtual Brain

The patient-specific network models are constructed using The Virtual Brain in order to verify the effectiveness of derived TZs. The six-dimensional model named Epileptor is specifically employed to describe a network node and the reconstructed structural connectivity is used to connect the nodes. The Epileptor is a phenomenological neural population model reproducing seizure characteristics, which consists of five state variables and six parameters. Each Epileptor is coupled with others via the permittivity coupling of slow time scales variable z replicating extracellular effects. In the equation below, $K_{ij}$ denotes the connection weight between node i and node j, and $\tau_{ij}$ represents the time delay determined by track length between the two nodes.

$$\dot{x}_{1,i} = y_{1,i} - f_1(x_{1,i}, x_{2,i}) - z_i + I_{1,i}$$

$$\dot{y}_{1,i} = 1 - 5(x_{1,i})^2 - y_{1,i}$$

-continued $$\dot{z}_i = \frac{1}{\tau_0}\left\{4(x_{1,i} - x_{0,i}) - z_i - \sum_{j=1}^{N} K_{i,j}(x_{1,j}(t-\tau_{ij}) - x_{1,i})\right\}$$

$$\dot{x}_{2,i} = -y_{2,i} + x_{2,i} - (x_{2,i})^3 + I_{2,i} + 0.002g(x_{1,i}) - 0.3(z_i - 3.5)$$

$$\dot{y}_{2,i} = \frac{1}{\tau_2}\{-y_{2,i} + f_2(x_{2,i})\}$$

where $$f_1(x_{1,i}, x_{2,i}) = \begin{cases} x_{1,i}^3 - 3x_{1,i}^2 & \text{if } x_{1,i} < 0 \\ \{x_{2,i} - 0.6(z_i - 4)^2\}x_{1,i} & \text{if } x_{1,i} \geq 0 \end{cases}$$

$$f_2(x_{2,i}) = \begin{cases} 0 & \text{if } x_{2,i} < -0.25 \\ 6(x_{2,i} + 0.25) & \text{if } x_{2,i} \geq -0.25 \end{cases}$$

$$g(x_{1,i}) = \int_{t_0}^{t} e^{-\gamma(t-\tau)}x_{1,i}(\tau)d\tau$$

Clinically, degrees of epileptogenicity may be mapped upon the excitability parameter $x_0$ where it is distinguished EZ that generates spontaneous seizure activities, propagation zone (PZ) that is recruited by seizure propagation from EZ, and other zones not recruited in the propagation. In this example, the excitability parameter $x_0$ is set to −1.6 for EZ, and a value between −2.150 and −2.095 corresponding to PZ for the all other nodes depending on structural connectivity of each patient, in order to simulate the worst-case scenario at which seizure activity originated from EZ propagates to most other brain nodes. For the other parameters in the equations, it is used $I_1$=3.1, $I_2$=0.45, $\gamma$=0.01, $\tau_0$=6667 and $\tau_2$=10. Also, zero mean white Gaussian noise with a standard deviation of 0.0003 is linearly added to the variables $x_2$ and $y_2$ in each Epileptor for stochastic simulations. These noise environments make each Epileptor excitable and thus produce interictal spikes, as a baseline activity.

Using the patient-specific network model, the seizure propagation characteristics before and after eliminating target nodes or target edges are simulated. In particular, it is quantified the suppression ratio of seizure propagation as equation below and it is used to compare the removal effect of each TZ. $x_1+x_2$ waveform of each Epileptor is observed to reproduce local field potential at each node.

$$SR, \text{ suppression ratio of seizure propagation} = \left(\frac{N_{bef} - N_{af}}{N_{bef}}\right) * 100(\%),$$

$N_{bef}$ being the number of seizure-recruited nodes before removal of TZs, $N_{af}$ the number of seizure-recruited nodes after removal of the TZs.

To assess normal brain function, a stimulation paradigm is adapted, in which it is quantified the information transmission capacity of the network through the spatiotemporal properties of the trajectory leading to its resting state, after a transient stimulation. 8 particular well-known RS networks are tested, which include default mode, visual, auditory-phonological, somato-motor, memory, ventral stream, dorsal attention and working memory. Simulating a specific brain region could reproduce dynamically responsive networks similar to brain activation patterns in RS networks.

The Table 1 below shows stimulus sites able to reproduce the best-matched response patterns with brain activation patterns in each RS network. The number in parentheses indicates the node index.

| Resting-state network | Stimulation sites |
| --- | --- |
| Default mode (DM) | ctx-lh-medialorbitofrontal (13) |
| | ctx-rh-medialorbitofrontal (62) |
| | ctx-lh-superiorfrontal (27) |
| | ctx-rh-superiorfrontal (76) |
| Visual (V) | ctx-lh-rostralanteriorcingulate (25) |
| Working Memory (WM) | ctx-rh-rostralanteriorcingulate (74) |
| Auditory-phonological (AP) | ctx-lh-superiortemporal (29) |
| | ctx-rh-superiortemporal (78) |
| Somato-motor (SM) | ctx-lh-precentral (23) |
| Dorsal attention (DA) | ctx-rh-precentral (72) |
| Memory (M) | ctx-lh-lateraloccipital (10) |
| | ctx-rh-lateraloccipital (59) |
| Ventral stream (VS) | ctx-lh-caudalanteriorcingulate (2) |
| | ctx-rh-caudalanteriorcingulate (51) |

It is chosen to apply an electrical pulse of 2.5 s to a particular cortical region and to observe the response signals in all brain regions. The stimulation sites to test each RS network are shown in Table 1. In this simulation, the patient-specific network models disclosed before are used, with the neural mass model of the generic 2-dimensional oscillator of equation (4) below rather than the Epileptor, in order to replicate damped oscillations due to the stimulation. For the parameters, τ=1, a=−0.5, b=−15.0, c=0.0, d=0.02, e=3.0, f=1.0 and g=0.0 are used. Each oscillator is coupled with other oscillators via difference coupling based on individual structural brain connectivity. Here, each oscillator, or brain node, operated at stable focus in proximity to the instability point, supercritical Andronov-Hopf bifurcation, but never reached the critical point. Each node shows no activity without stimulation, but when stimulated (or received input from other nodes through connectome), it generates a damped oscillation by operating closer to the critical point. Since the working distance to the critical point is determined depending on each node's connectivity (connection weights and time delays), each node generates different damped oscillations with different amplitudes and decay times, thereby producing a specific energy dissipation pattern (responsive activation pattern) according to the stimulation location and brain connectivity.

$$\dot{v}_I = d\tau\left(-fv_i^3 + ev_i^2 + gv_i + w_i + \sum_{j=1}^{N} K_{ij}(v_i(t-\tau_{ij}) - v_i)\right)$$

$$\dot{w}_I = \frac{d}{\tau}\left(cv_i^2 + bv_i - w_i + a\right)$$

Then, the responsive spatiotemporal activation patterns are compared before and after removing target nodes or target edges. To do so, the subspace is quantified, in which a trajectory evolves after stimulation, by employing mode level cognitive subtraction (MLCS) analysis. From the principal component analysis (PCA) using response signals in all brain nodes before in-silico surgery, a reference coordinate system is derived, i.e., eigenvectors $\varphi_n$ of covariance matrix of response signals were calculated. Then, three principal components (PC) are selected and response signals in both cases (before and after removal of TZ, $q_b$, $q_a$) are projected upon the PC, reconstructed responsive signals $q_{r,b}$, $q_{r,a}$ are obtained at each brain node:

$$q_{r,b} = \sum_{n=1}^{3} \varphi_n \eta_{n,b}(t), \; \eta_{n,b}(t) = \varphi_n^T q_b \quad (5)$$

$$q_{r,a} = \sum_{n=1}^{3} \varphi_n \eta_{n,a}(t), \; \eta_{n,a}(t) = \varphi_n^T q_a$$

To compare the reconstructed responsive patterns, the amount of overlap between the powers of the reconstructed response signals are calculated before and after eliminating TZ, for every brain node. The obtained value in each brain node is normalized by the overlap value using only the signal power before removal of TZ, and then defined as the similarity coefficient (defined as 1—the deviation from 1, if the value>1; thereby, the similarity coefficient has a value between 0 and 1). Here, it is considered that the derived TZ has a high risk if the mean value of similarity coefficients in all brain regions is below 0.75. In other words, it indicates that the elimination of the TZ could affect the corresponding RS network. It is referred to the TZ with high risk as inoperable zone. If the TZs contain more than one node, it is figured out the critical node that severely changed the responsive activation patterns due to stimulation, and then designated that node as inoperable zone. The critical node is defined as a node that yields the lowest similarity coefficients when the same simulation is repeated after removing each node belonging to the TZ. The updated inoperable zone (added the critical node) is applied to the modularity analysis again, which results in a new TZ. The effectiveness and safety of the newly obtained TZ are evaluated through network simulations again. These feedback procedures are iterated until the TZs that meets the safety criteria are acquired.

Example 2: Target Zone Derivation

In this example, several surgical intervention options outside the EZ are presented for a particular patient. This patient has two EZs, ctx-rh-lingual (node 61) and ctx-rh-parahippocampal (node 64), and these two EZs are designated as inoperable zone.

Using modularity analysis, a patient-specific modular structure is constructed considering inoperable zones that are identified in FIG. 2A. The brain network nodes are divided into 7 modules with a modularity coefficient of 0.3912, and the green module, including the EZs, is further subdivided into 4 sub-modules. Based on this modular structure, 3 target nodes (black triangles) and 8 target edges (gray dotted lines), connecting the EZ sub-module to other sub-modules or modules, are identified. The anatomical location of the initial TZs are shown in FIG. 2B.

In the network simulation for evaluating the effectiveness of the TZs, before the removal of TZs, most brain nodes are recruited after the EZs generate a seizure activity. However, when 3 target nodes are removed, the seizure activity is almost isolated in EZs with a suppression ratio of seizure propagation SR of 95.65%. When 8 target edges are disconnected, seizure-recruited nodes are significantly reduced with the SR of 91.30%, even though the seizure activity is still observed in several neighboring nodes of EZs. These results demonstrate that the elimination of the derived TZs is able to prevent seizure propagation. Meanwhile, in the network simulation for evaluating the safety of the TZs, similarity coefficients between responsive activation patterns are calculated before and after removal of the TZs, by stimulating specific brain regions to test several RS networks as shown in FIG. 3A. Low similarity coefficients indicate that the response pattern due to stimulation has been severely changed after removing the TZs. In this case, the results imply that the elimination of the obtained TZs could lead to a larger network disorganization and then a higher risk for negative cognitive impact, in particular for memory function. The TZs are considered unsafe, if removal of the TZs deforms the response pattern to more than 25% of the original pattern, i.e. if the mean value of similarity coefficients in all brain regions is below 0.75.

Since the obtained TZs may have a negative impact on the memory network, the next step is to identify the critical node that leads to the most significant variation. FIG. 3B presents the effect on the memory network when each node among the initially derived target nodes is removed. Eliminating the left-cerebellum-cortex (node 35) yields the lowest mean similarity value compared to before removal (0.58, when the stimulus is applied to node 10), so that this node is defined as a critical node, and therefore designated as inoperable zone.

By feeding back the updated inoperable zones to modularity analysis, a new modular structure is obtained. FIG. 2C shows the modular structure when the critical node (gray triangle, node 35) as well as two EZs (nodes 61 and 64) are set to inoperable zones. The brain network nodes are divided into eight modules with modularity coefficient of 0.3995, and the green module including EZs is subdivided into two sub-modules so that each inoperable zone and its neighboring nodes belong to the same sub-module. Based on this modular structure, new target nodes (black triangles) and target edges (gray dotted lines) are acquired. Anatomical location of the new TZs are shown in FIG. 2D.

FIG. 4 shows network simulation results for effectiveness evaluation of newly derived TZs. The results present time series data, i.e. local field potentials, in all brain nodes. Before the removal of the TZs, the seizure activity originated from the EZs propagates to other nodes after some delay, i.e. most nodes are seizure-recruited as shown in FIG. 4A. Having eliminated the new TZs, a significant reduction of seizure-recruited regions is identified compared to pre-removal simulation even though they have some more seizure-recruited regions than when removing initial TZs. As shown in FIGS. 4B and 4C, the SR after removing 3 new target nodes is of 89.86%, and the SR after removing 5 new target edges is of 85.51%. FIG. 4D shows the simulation results when removing the same number of random nodes, excluding the EZs, as the derived target nodes. Comparing the degree of reduction in seizure-recruited nodes, it demonstrates that the elimination of the TZs obtained from the proposed method can effectively suppress the seizure propagation. In this example, the SR after removing 3 random nodes is of 31.88%. Meanwhile, the simulation results show that persistent spikes occur even if seizure activity is suppressed in each brain node after the removal of TZ. These interictal spikes are caused by the noise environment that is applied for stochastic simulations. Gaussian noise is applied to all brain nodes (Epileptors) to account for background internal activity, so that each node generates random spike events as a baseline activity. The occurrence of these spikes is regulated according to the state of each node, such as preictal, ictal and postictal.

FIG. 5 shows the difference between the safety evaluation results for initial TZs and new TZs. The histogram shows the mean value of the similarity coefficients between the response patterns due to stimulation in all brain regions before and after removal of the TZs. Comparing the values between two groups, it indicates that eliminating the new TZs is able to maintain all RS networks at a similar level as before removal (the mean value of similarity coefficients>0.75), whereas eliminating the initial TZs may disrupt memory network. In other words, this means that the newly derived TZs have less impact on the transmission properties of the brain network sustaining normal brain function. The results also show that disconnecting the fiber tracts corresponding to the target edges has less impact on normal brain function than resecting the brain regions corresponding to the target nodes. In this example, the new TZs obtained from a single feedback satisfy the safety criteria. However, if the newly derived TZs do not satisfy the criteria, the iterative feedback procedure (find a critical node among the new TZs; set it to inoperable zone; and obtain a new modular structure) continues until the TZs that meet the criteria are derived.

Only the results when the resolution parameter in the modularity analysis is fixed to 1.25 are presented in this Example in FIGS. 2 to 5 in order to easily describe the process of deriving TZs. However, since the proposed method involves a parameter sweep of the resolution parameter of 0.5 to 1.5 with intervals of 0.25, multiple modular structures are obtained according to the parameter value (the resolution parameter determines the size of each module, i.e. the number of modules), resulting in multiple TZs options. For the particular patient of this Example, 5 variants for the target node and 7 variants for the target edge are initially obtained. After applying the feedback, 7 variants for the target node and 9 variants for the target edge are finally derived.

Example 3: Systematic Analysis According to an Epileptogenic Zone Location

In order to demonstrate the robustness of the proposed method, additional simulation results are presented, that show how the TZs vary according to the location of the EZs. FIGS. 6A and 6B show target nodes and target edges, in another specific patient, that are obtained by performing systematic simulations where one EZ is placed in all possible brain nodes, the EZ being assumed to be an inoperable zone. The cumulative results of TZs identify the nodes and the edges that are frequently used as TZs. Frequently acquired nodes and edges play an important role in propagating seizure activity from the localized region to the entire brain, and can effectively control seizure propagation by being removed. In this patient, the most frequently derived node is ctx-rh-postcentral (node 70), and the most frequently derived edge is the connection between ctx-lh-supramarginal (node 30) and ctx-lh-postcentral (node 21). Anatomical locations of cumulative results are presented in FIG. 6C. Meanwhile, in deriving the TZs, the frequency of the target nodes initially acquired is positively correlated with the node strength (the sum of weights of links connected with other nodes), i.e., the nodes having high strength are frequently derived as TZs (correlation coefficient: 0.7842). However, the final target nodes obtained from the feedback procedure tend to be more concentrated at a few nodes, and thus the frequency finally acquired target nodes is not noticeably relevant to the node strength, the correlation coefficient being of 0.3059.

The critical nodes, which are used for the feedback strategy to consider the safety for normal brain functions, are not significantly different in all patients. In particular, the superior-frontal cortex (nodes 27 and 76) appears often as the critical node, which means that these nodes are effective to control seizure propagation but removing them may cause a problem for the normal brain function. The network simulation results identify that the elimination of those nodes severely distort the RS networks corresponding to visual, working memory and ventral stream as well as default mode. In fact, the superior-frontal cortex has been investigated as a node that is frequently used as the shortest path connecting two different brain nodes, and also has been shown to play an important role in interhemispheric propagation of seizures.

The invention claimed is:

1. A method of identifying a potentially surgically operable target zone in an epileptic patient's brain comprising:
providing a computerized platform modelling various zones of a primate brain and connectivity between said zones;
providing a model of an epileptogenic zone and a model of the propagation of an epileptic discharge from an epileptic zone to a propagation zone, the model of the epileptogenic zone being a mathematical model describing the onset, the time-course and the offset of the epileptic discharge, and loading said models in the computerized platform to obtain a computerized platform modelling an epileptic primate brain;
identifying an estimated epileptogenic zone in the patient's brain;
personalizing the computerized platform modelling the epileptic primate brain according to the patient's brain structural connectivity and parametrizing the estimated epileptogenic zone, in said computerized platform, as an epileptogenic zone, to obtain a patient's personalized computerized platform;
carrying out a modularity analysis with the patient's brain structural connectivity to derive potential target zones acting as hubs in the interaction between modules, said potential target zones being outside the potential epileptogenic zone and such as, if they are surgically opered or removed, are minimizing epileptic seizure propagation, and evaluating the potential target zones' effectiveness to minimize propagation of epileptic seizures by network simulation simulating propagation characteristics of said epileptic seizures in the personalized patient's computerized platform and identifying one or more effective target zones, said effective target zones being outside the epileptogenic zone and such as, if they are surgically operated, are minimizing seizure propagation;
evaluating the potential target zones' safety to maintain normal brain functions by network simulation wherein simulated spatiotemporal brain activation patterns in a defined state condition are obtained from the personalized computerized platform before and after removal of said zone and these simulated spatiotemporal brain activation patterns obtained before removal of the zone are compared with the simulated spatiotemporal brain activation patterns obtained after removal of the zone and, if the spatiotemporal brain activation patterns obtained before removal of the zone are substantially the same as the spatiotemporal brain activation patterns obtained after removal of the zone, then identifying said potential target zone as a safe target zone; and
identifying the potential target zones which satisfy both effectiveness and safety evaluation criteria as potentially surgically operable target zones.

2. The method of claim 1, wherein the estimated epileptogenic zone in the patient's brain is estimated clinically.

3. The method of claim 1, wherein the target zones are nodes or edges involved in the epileptic seizure propagation said nodes and edges corresponding to brain regions and fiber tracts between brain regions, respectively.

4. The method of claim 1, wherein the structural connectivity is reconstructed from images data of the patient brain acquired using magnetic resonance imaging or diffusion-weighted magnetic resonance imaging.

5. The method of claim 1, wherein the computerized platform modelling the epileptic primate brain is personalized according to the patient-specific brain connectivity and functional data of the patient.

6. The method of claim 5, wherein the functional data are acquired through electroencephalography (EEG) or stereotactic EEG (SEEG) techniques.

7. The method of claim 1, wherein, for the implementation of the modularity analysis, a constraint is added in order to prevent inoperable nodes from being derived as target zones.

8. The method of claim 1, wherein systematic simulations are carried out in the patient's personalized computerized platform, and wherein, if a target zone does not satisfy the evaluation criteria, a new target zone is derived by feeding back the simulation results to the analysis again.

9. The method of claim 1, wherein the defined state condition is the resting state condition.

10. The method of claim 9, wherein a plurality of resting states conditions are used for simulation.

11. The method of claim 1, wherein the modularity analysis provides a non-overlapping modular structure that minimizes edges between modules and maximizes edges within modules.

12. The method of claim 2, wherein the target zones are nodes or edges involved in the epileptic seizure propagation said nodes and edges corresponding to brain regions and fiber tracts between brain regions, respectively.

13. The method of claim 2, wherein the structural connectivity is reconstructed from images data of the patient brain acquired using magnetic resonance imaging or diffusion-weighted magnetic resonance imaging.

14. The method of claim 3, wherein the structural connectivity is reconstructed from images data of the patient brain acquired using magnetic resonance imaging or diffusion-weighted magnetic resonance imaging.

15. The method of claim 2, wherein the computerized platform modelling the epileptic primate brain is personalized according to the patient-specific brain connectivity and functional data of the patient.

16. The method of claim 3, wherein the computerized platform modelling the epileptic primate brain is personalized according to the patient-specific brain connectivity and functional data of the patient.

17. The method of claim 4, wherein the computerized platform modelling the epileptic primate brain is personalized according to the patient-specific brain connectivity and functional data of the patient.

18. The method of claim 15, wherein the functional data are acquired through electroencephalography (EEG) or stereotactic EEG (SEEG) techniques.

19. The method of claim 16, wherein the functional data are acquired through electroencephalography (EEG) or stereotactic EEG (SEEG) techniques.

20. The method of claim 17, wherein the functional data are acquired through electroencephalography (EEG) or stereotactic EEG (SEEG) techniques.

* * * * *